(12) United States Patent
Thakkar et al.

(10) Patent No.: US 10,537,606 B2
(45) Date of Patent: Jan. 21, 2020

(54) PHYTO-ACTIVE BASED ANTI-CANCER FORMULATION

(71) Applicant: OMNI CURE LTD., East Sussex (GB)

(72) Inventors: Jatin Thakkar, Mumbai (IN); Gisli Örn Lárusson, London (GB)

(73) Assignee: OMNI CURE LTD., East Sussex (GB)

( * ) Notice: Subject to any disclaimer, the term of this patent is extended or adjusted under 35 U.S.C. 154(b) by 437 days.

(21) Appl. No.: 15/320,548

(22) PCT Filed: Jan. 6, 2015

(86) PCT No.: PCT/IB2015/050084
§ 371 (c)(1),
(2) Date: Dec. 20, 2016

(87) PCT Pub. No.: WO2015/193741
PCT Pub. Date: Dec. 23, 2015

(65) Prior Publication Data
US 2017/0196929 A1    Jul. 13, 2017

(30) Foreign Application Priority Data

Jun. 20, 2014 (IN) .......................... 2003/MUM/2014

(51) Int. Cl.

| | |
|---|---|
| *A61K 36/9066* | (2006.01) |
| *A61K 36/87* | (2006.01) |
| *A61K 36/324* | (2006.01) |
| *A61K 9/00* | (2006.01) |
| *A61K 45/06* | (2006.01) |
| *A61K 31/01* | (2006.01) |
| *A61K 31/05* | (2006.01) |
| *A61K 31/12* | (2006.01) |
| *A61K 31/56* | (2006.01) |

(52) U.S. Cl.
CPC ........ *A61K 36/9066* (2013.01); *A61K 9/0053* (2013.01); *A61K 31/01* (2013.01); *A61K 31/05* (2013.01); *A61K 31/12* (2013.01); *A61K 31/56* (2013.01); *A61K 36/324* (2013.01); *A61K 36/87* (2013.01); *A61K 45/06* (2013.01)

(58) Field of Classification Search
CPC ............ A61K 2300/00; A61K 36/9066; A61K 36/324; A61K 36/87; A61K 45/06; A61K 31/01; A61K 31/05; A61K 31/12; A61K 31/353; A61K 31/56; A61K 31/69; A61K 31/7008; A61K 31/7048; A61K 31/737; A61K 36/235; A61K 38/39; A61K 9/0053; A61K 36/00; A61K 36/185; A61K 36/48
See application file for complete search history.

(56) References Cited

PUBLICATIONS

Ranade SY and Gaud RS "Current Strategies in Herbal Drug Delivery for Arthritis: An Overview" IJPSR, Oct. 1, 2013; vol. 4(10): 3782-3794. (Year: 2013).*
C Gorman, et al "Te Hype and the Hope" Time (1998) 151(19). pp. 40-44. (HTML copy pp. 1-9). (Year: 1998).*
GB Dermer "Another Anniversary for the War on Cancer" Bio/Technology Mar. 12, 1994. p. 320. (Year:1994).*
R McKie "Cancer Research Set Back a Decade" The Observer Jun. 10, 2001. pp. 1-4. (Year: 2001).*
T Gura "Systems for Identifying New Drugs are Often Faulty" Science (1997) 278 (Nov. 7). pp. 1041-1042. (Year: 1997).*

* cited by examiner

*Primary Examiner* — Aaron J Kosar
(74) *Attorney, Agent, or Firm* — Scarinci Hollenbeck, LLC; Libby Babu Varghese (57) ABSTRACT

The present disclosure relates to a formulation for preventing and treating cancer which avoids the undesirable side effects observed when using the conventional therapies. The formulation in accordance with the present disclosure comprises a formulation having active constituents comprising a combination of extracts from *Boswellia* spp, *Curcuma longa* and *Vitis vinifera*.

12 Claims, 7 Drawing Sheets

PHYTO-ACTIVE BASED ANTI-CANCER FORMULATION

FIELD

The present disclosure relates to a phyto-active based formulation for treating cancer.

BACKGROUND

Conventionally, treatment of cancer following detection is carried out by radiation therapy, immunotherapy, chemotherapy, surgical interventions and monoclonal antibody therapy. The therapy depends upon the location of the tumor and the stage of disease. Radiotherapy can also destroy the adjoining healthy cells, chemotherapy results in a number of serious side effects including hair fall, nausea, loss of appetite, and the like. The surgical methods require great expertise and sterile conditions, which makes the procedures extremely costly and out of the reach of most of the people.

Certain plant based extracts, isolated compounds and aromatic oils have shown positive activities against cancer cell. These compounds can act directly against cancer cells by acting on target sites. They can also act by arresting the process of inflammation; which plays a significant role in establishing the primary pathology in various diseases. Scientific studies have highlighted that the resinous gum from *Boswellia* spp.; a small tree available in the tropics of Asia effectively controls joint swellings and helps to subdue the problems of arthritic conditions. The efficacy is primarily due to a group of compounds—Boswellic acids, present in the *Boswellia* spp. Boswellic acids (BAs) inhibit leukotriene synthesis and thus, exhibit anti-inflammatory action. Keto boswellic acid (KBA) and Acetyl Keto boswellic acid (AKBA) are the two important acids which are responsible for control of the inflammation. These compounds may also be effective against various other life threatening diseases.

U.S. Pat. No. 7,455,860 suggests a phytochemical dietary supplement and therapeutic composition capable of treating and controlling inflammatory diseases and cancer. The composition of U.S. Pat. No. 7,455,860 comprises 2-30% by weight of a standardized *Boswellia serrata* extract containing at least 30% of 3-O-acetyl-11-keto-β-boswellic acid (AKBA); glucosamine salt and 5-30% by weight of curcuminoid salt. The composition also comprises an optional ingredient selected from bromelain, chondroitin, methylsulphonylmethane, resveratrol, extracts of white Willow and ginger, and quercetin. It is however, observed that use of glucosamine in higher doses may damage pancreatic cells, possibly increasing the risk of developing diabetes.

U.S. Pat. No. 8,192,768 suggests a composition for treating 5-lipoxygenase mediated diseases and free radical mediated diseases with an effective amount of *Boswellia serrata* extract containing 3-O-acetyl-11-keto-β-boswellic acid (AKBA) and an effective amount of enriched demethylated curcuminoids obtained from a *Curcuma longa* extract; and an optional ingredient. The composition of U.S. Pat. No. 8,192,768 uses enriched actives in the composition.

Accordingly, there is a need for an effective, low cost and easily available phyto-active based cure for cancer, with no or very low side effects.

OBJECTS

Some of the objects of the present disclosure, which at least one embodiment herein satisfies, are as follows:

It is an object of the present disclosure to provide a phyto-active based formulation to arrest the proliferation of cancer cells.

It is still another object of the present disclosure to provide a phyto-active based formulation to enhance/support the therapeutic efficacy of an existing drug.

It is yet another object of the present disclosure to provide a phyto-active based formulation to arrest the proliferation of cancer cells, with the formulation having low side effects.

It is another object of the present disclosure to provide a method for the prevention and/or treatment of cancer.

It is another object of the present disclosure to provide the use of a formulation for the prevention and/or treatment of cancer.

Other objects and advantages of the present disclosure will be more apparent from the following description which is not intended to limit the scope of the present disclosure.

SUMMARY

In accordance with one aspect of the present disclosure there is provided a formulation for the prevention and/or treatment of cancer; said formulation having active constituents comprising a combination of: *Boswellia* spp extract in an amount ranging from 60 to 80 wt % of actives; *Curcuma longa* extract in an amount ranging from 10 to 30 wt % of actives; and *Vitis vinifera* extract in an amount ranging from 5 to 20 wt % of actives.

In another aspect of the present disclosure there is provided a method for the prevention and/or treatment of cancer by orally administering to a subject a therapeutically effective amount of a formulation having active constituents comprising a combination of: *Boswellia* spp extract in an amount ranging from 60 to 80 wt % of actives; *Curcuma longa* extract in an amount ranging from 10 to 30 wt % of actives; and *Vitis vinifera* extract in an amount ranging from 5 to 20 wt % of actives.

In still another aspect of the present disclosure there is provided a use of a formulation for the prevention and/or treatment of cancer.

BRIEF DESCRIPTION OF THE ACCOMPANYING DRAWINGS

The process of the present disclosure will now be described with the help of the accompanying drawings, in which.

DETAILED DESCRIPTION

Conventional modes of therapy for cancer include radiation therapy, chemotherapy, hormonal therapy and surgery. The drugs given during chemotherapy are very powerful and as a result have undesirable and serious side effects like nausea, vomiting, fatigue, pain, diarrhea, constipation, blood disorders, nerve damage, hair loss, appetite loss, and such. Radiation therapy and hormone therapy can also cause many side effects.

Accordingly, the present disclosure provides a formulation for the prevention and treatment of cancer which avoids these undesirable side effects. The plants included in the formulation of the present disclosure are selected for optimum therapeutic effect and at the same time the formulation does not cause the undesirable side effects.

In one aspect, the present disclosure provides a phyto-active based formulation to arrest proliferation of cancerous cells having active constituents comprising a combination of extracts from *Boswellia* spp, *Curcuma longa*, and *Vitis vinifera*.

In an embodiment of the present disclosure, the *Boswellia* spp extract is present in an amount ranging from 60 to 80 wt % of the actives. The *Boswellia* spp extract comprises 60 to 65% boswellic acid, and 5 to 20% limonene—blended together and used in the formulation of the present disclosure. The boswellic acid of the present disclosure is at least one selected from the group consisting of acetyl keto boswellic acid (AKBA), keto boswellic acid (KBA) and a combination thereof. The *Boswellia* spp extract may also comprise other aromatics like myrcene. In an embodiment of the present disclosure, the amount of AKBA and KBA in the Boswellic acid ranges from 30 to 40%.

Keto boswellic acid (KBA) and acetyl Keto boswellic acid (AKBA) from the boswellic acids group have shown, to be effective in arresting the growth of cancerous cells. AKBA helps to control the inflammation process which is the main trigger in chronic disease processes, and thus AKBA is able to stop the growth of cancer cells. Limonene and myrcene are able to effectively subdue the malignant features of cancer cells, promotes death of cancer cells and prevent metastatic changes taking place during the spread of cancer.

In another embodiment of the present disclosure, the *Curcuma longa* extract is present in an amount ranging from 10 to 30 wt % of the actives. The *Curcuma longa* extract is enriched with 85 to 95% curcuminoids.

In another embodiment of the present disclosure, the *Vitis vinifera* extract is present in an amount ranging from 5 to 20 wt % of actives. The *Vitis vinifera* extract comprises 20 to 40% polyphenol, preferably resveratrol, which is short-listed as a marker because of its multi-faceted therapeutic potential.

Curcuminoids from *Curcuma longa* extract and resveratrol from *Vitis vinifera* extract demonstrate supportive role in the treatment of diseases caused by hyperactive oxidation, by improving body's own capacity to fight against disease attack. Curcuminoid interferes in the pathways involved in cancer development by blocking latent or chronic inflammatory reactions. Polyphenols, particularly resveratrol from *Vitis vinifera* have an inhibitory effect on the growth of various types of cancer cells.

In an exemplary embodiment of the present disclosure, the *Boswellia* spp extract is present as 70 wt % of actives; *Curcuma longa* extract is present as 20 wt % of actives; and *Vitis vinifera* extract as 10 wt % of actives.

*Boswellia* species are moderate-sized flowering plants, including both trees and shrubs and are native to tropical regions of Africa and Asia. The greatest diversity of *Boswellia* species are present in the Arabian Peninsula (Oman, Yemen), Northeastern Africa (Somalia) and Pakistan. *Curcuma longa* is a rhizomatous herbaceous perennial plant of the ginger family, Zingiberaceae, native to Southeast Asia. *Vitis vinifera* is native to the Mediterranean region, central Europe, and Southwestern Asia, from Morocco and Portugal North to Southern Germany and East to Northern Iran. Extracts from these plants are commercially available, and can be extracted from the plant materials by known processes such as solvent extraction, cryogenic extraction, hot continuous extraction (soxhlet), aqueous alcoholic extraction by fermentation, counter-current extraction, ultrasound extraction (sonication), supercritical fluid extraction and the like. The extraction is carried out from a suitable part of the plant including but not limited to rhizome, fruit (dried/pulp), bark, root, resin, leaf, seed, flower and stem.

The formulation of the present disclosure can be administered in a dosage form selected from the group consisting of a tablet, a capsule, liquid, syrup, powder, a pill, a lozenge and a pastille. In an exemplary embodiment of the present disclosure, the dosage form is in the form of a soft gelatin capsule.

The dose of the formulation of the present disclosure ranges from 750 to 1500 mg, administered 2 to 3 times per day.

The different plant species used in the present disclosure exhibit a synergistic effect, enhancing the therapeutic effect without displaying the undesirable side effects of the conventional anti-cancer therapies.

The extracts used in the present disclosure are effective in, controlling the release of pro-inflammatory cytokines, arresting the proliferation of cancerous cells; accelerating the process of apoptosis and enhancing/supporting the therapeutic efficacy of existing drug. While KBA and AKBA are effective in arresting the growth of cancerous cells besides stalling the inflammatory phenomenon, Curcuminoid and Resveratrol not only contribute in checking cancerous growth but also improve the body's capacity to fight against diseases.

Preliminary studies of the formulation of the present disclosure have shown that the formulation can be used effectively for the treatment of different types of cancer including but not limited to prostate cancer, breast cancer, uterine cancer, ovarian cancer, lung cancer and kidney cancer. The formulation is effective in preventing metastasis in patients diagnosed with cancer. Use of the formulation is effective in preventing relapse of the cancer. The formulation of the present disclosure results in an improved quality of life for the patients diagnosed with cancer.

The formulation of the present disclosure can also be used along with the conventional therapies of cancer cure, to achieve enhanced therapeutic effect.

In another aspect of the present disclosure there is provided a method for the prevention and/or treatment of cancer by orally administering a therapeutically effective amount of a formulation having active constituents comprising a combination of: *Boswellia* spp extract in an amount ranging from 60 to 80 wt % of actives; *Curcuma longa* extract in an amount ranging from 10 to 30 wt % of actives; and *Vitis vinifera* extract in an amount ranging from 5 to 20 wt % of actives. The therapeutically effective amount of the formulation is 750 to 1000 mg and is administered 3 to 4 times per day. The dosage of the formulation in accordance with the present disclosure is 12.5 mg per kg of body weight 3 to 4 times per day. The dosage form of the formulation is selected from the group including but not limited to a tablet, a capsule, liquid, syrup, powder, a pill, a lozenge and a pastille. The preferred dosage form for the formulation in accordance with the present disclosure is soft gelatin capsule.

In another aspect of the present disclosure there is provided a use of a formulation having active constituents comprising a combination of: *Boswellia* spp extract in an amount ranging from 60 to 80 wt % of actives; *Curcuma longa* extract in an amount ranging from 10 to 30 wt % of actives; and *Vitis vinifera* extract in an amount ranging from 5 to 20 wt % of actives, for the prevention and/or treatment of cancer.

In an embodiment of the present disclosure the formulation can be used for the treatment of cancer including but not limited to prostate cancer, breast cancer, uterine cancer, ovarian cancer, lung cancer and kidney cancer.

The formulation is used for the prevention and/or treatment of cancer by orally administering a therapeutically effective amount of the formulation 3 to 4 times per day. The therapeutically effective amount of the formulation in accordance with the present disclosure is 750 to 1500 mg.

In another aspect of the present disclosure the active constituents from a combination of *Boswellia* spp extract in an amount ranging from 60 to 80 wt % of actives; *Curcuma longa* extract in an amount ranging from 10 to 30 wt % of actives; and *Vitis vinifera* extract in an amount ranging from 5 to 20 wt % of actives is used for the manufacture of a medicament for the prevention and/or treatment of cancer.

The extracts are commercially available and can also be extracted from the plant materials by known processes such as solvent extraction, cryogenic extraction, hot continuous extraction (soxhlet), aqueous alcoholic extraction by fermentation, counter-current extraction, ultrasound extraction (sonication), supercritical fluid extraction and the like. The extraction is carried out from a suitable part of the plant including but not limited to rhizome, fruit (dried/pulp), bark, root, resin, leaf, seed, flower and stem.

The present disclosure is further described in the light of the following non-limiting examples which is set forth for illustration purpose only and not to be construed for limiting the scope of the disclosure.

EXAMPLE 1: Constituents and Plant Part Used in the Formulation

Table-1 below depicts the constituents, plant parts and quantity used in the formulation of the present disclosure.

EXAMPLE 2: Acute Oral Toxicity (Oral $LD_{50}$) of the Formulation

Single dose acute oral toxicity (oral $LD_{50}$) in mice was provided by Toxicological Research & Testing Laboratories Pvt. Ltd., Navi Mumbai. The study was carried out on Swiss Albino mice (Bharat Serums & Vaccines Ltd., Thane) aged 6 to 8 weeks. Five mice of each gender per dose were used for the study. The animals were identified by the cage number and the individual markings on the fur. They were provided a Standard 'Amrut' brand pelleted rat feed (Pranav Agro Industries Ltd., Sangli), ad libitum. Clean tap water was provided in a glass container, ad libitum. The mice were housed gender-wise, 5 per cage in polypropylene cages with stainless steel grill tops facilities for food and water bottle, and bedding of clean paddy husk. The temperature was maintained between 23 to 25° C. and relative humidity between 50 to 70%; 12 hours each of dark and light cycle was maintained.

Sixty mice, weighing between 22.90 to 27.00 g, were divided into 6 groups, each comprising 5 mice of each gender. Animals were allowed an acclimatization period of 7 days to the laboratory conditions prior to initiation of study. Animals were assigned to cages and groups, five per cage, sex-wise and the individual animal was fur marked.

The formulation was administered by oral route, as it is the route of administration intended for use in humans.

The contents of the formulation were suspended in distilled water with 0.5% tween 80 and were administered to mice at the dose levels: of 250 mg/kg (Group II), 500 mg/kg Group III), 1000 mg/kg (Group IV), 1500 mg/kg (Group V), and 2000 mg/kg (Group VI), respectively. A separate group (Group I) comprising of 5 males and 5 females received the vehicle alone, in equivalent volume and acted as a control group. The suspensions of the test article were prepared in concentrations that allowed their administration in a constant volume of 0.2 ml/10 g bodyweight of the animals, for each of the five dosages used.

The animals were observed at hourly intervals for the first 6 hours after the formulation was administered and then at the end of every 24 hours for 14 days, for clinical signs and symptoms, and mortality, if any. The time of onset, and duration of these symptoms, was recorded. The body weight of each animal was recorded on day 0 and at weekly intervals for all the surviving animals. The group mean data were calculated and compared.

All the animals were sacrificed at the end of the observation period of 14 days, and were subjected to a detailed necropsy.

No signs of toxicity or mortality were recorded during the entire observation period of 14 days in any of the five groups of animals on administration of a single oral dose of the test

TABLE 1

| S. No. | Botanical name of Plant Used | Indian Name of the Constituent | Part used in extraction | Ref. Book | Qty/Cap (mg) | Raw Material form used in formulation |
|---|---|---|---|---|---|---|
| 1 | *Boswellia* spp. | Salai guggulu | Dry Resin | BPN | 525 | Exts. 30% AKBA & Limonene NLT 15% |
| 2 | *Curcuma longa* | Haridra | Rhizome | BPN | 150 | Ext. Curcuminoids 90% |
| 3 | *Vitis vinifera* | Draksha | Fruit | BPN | 75 | Ext. Polyphenol 30% | article in the dosages employed in the respective groups. The animals in the Control group also did not show any toxicity or mortality.

Since the maximum dose of 2000 mg/kg that was administered in a single oral gavage to mice, did not produce any mortality, the $LD_{50}$ of the formulation could not be determined. The median lethal dose ($LD_{50}$), by oral route in mice, for the formulation is therefore, >2000 mg/kg. It was therefore, concluded that the formulation exhibits a very low acute toxicity on oral dosing in mice. Therefore, the formulation can be considered safe for therapeutic use in humans, in recommended oral therapeutic doses and regimen.

Surviving animals from all treated groups II, III, IV, V and VI exhibited similar weight gain as observed in the control group throughout the observation period of 14 days following the administration of the dose.

Pathological changes or any clinical signs of toxicity were not observed in any of the treated animals in any of the dose groups, after detailed necropsy.

EXAMPLE 3: HPLC Analysis

The active ingredients (resveratrol, *Curcuma longa* dry extract, *Boswellia* spp extract,) of the formulation were analyzed. The standards used were: Resveratrol (Sigma Aldrich), Curcumin: (In-house), AKBA (K. Patel Phyto Extracts Pvt. Ltd.)

EXAMPLE 3A: Analysis of Resveratrol

Step-1: 10 mg of Resveratrol standard (Sigma Aldrich) was weighed and transferred into a 100 ml volumetric flask. 80 ml of ethanol was added, shaken well to dissolve and the volume was made up with ethanol to get a solution having a concentration of about 100 µg/ml of Resveratrol.

Step-2: 10 mg of Resveratrol (active ingredient, N. No. 14F00859) was weighed and transferred into a 100 ml volumetric flask. 80 ml of ethanol was added, shaken well to dissolve and the volume was made up with ethanol to get a solution having a concentration of about 100 µg/ml of Resveratrol.

Step-3: 1 g of red wine extract (B. No. 0131117) was weighed in a 100 ml beaker. 25 ml of ethanol was added and the solution was sonicated for 10 minutes. After sonication, the solution was filtered through Whatman No 1 filter paper and the volume was made up to 25 ml by ethanol.

Step-4: Five Soft Gel Capsules were weighed, then pricked and placed in a 500 ml beaker. 200 ml of ethanol was added to the beaker. The solution was sonicated for 10 minutes followed by stirring on a magnetic stirrer for 60 minutes. The solution was filtered through Whatman No 1 filter paper and the volume was made up to 250 ml using ethanol.

Phenomenex Gemini $C_{18}$ column (250×4.6 mm, 5µ ID) was used for HPLC analysis.

Mobile phase-A: a solution was prepared by dissolving 0.136 g of potassium dihydrogen orthophosphate in 500 ml of water, 0.5 ml of orthophosphoric acid was added and diluted to 1000 ml with water;

Mobile phase-B: Acetonitrile

A linear gradient program using the conditions given below was used to conduct the assay:

Flow rate: 1.5 ml per minute
Detection wavelength: 310 nm
Injection volume: 20 µl The HPLC chromatograms of the standard and samples are illustrated in FIGS. 1A, 1B, 1C and 1D. Resveratrol was identified by its characteristic retention time.

EXAMPLE 3B: Analysis of Curcumin

Step-1: 10 mg of Curcumin standard (In-house) was weighed and transferred into a 100 ml volumetric flask. 80 ml 0.1% w/v methanolic sodium carbonate was added, shaken well to dissolve and the volume was made up with methanol to get a stock solution having a concentration of 100 µg/ml of Curcumin. From the stock solution, 2 ml was pipetted out in to a 100 ml volumetric flask and the volume was made up by methanol to obtain a concentration of 2 µg/ml solution of Curcumin.

Step-2: 10 mg of *Curcuma longa* Dry Extract (B. No. JW 004/13-14) was weighed and transferred into a 100 ml volumetric flask. 80 ml 0.1% w/v methanolic sodium carbonate was added, shaken well to dissolve and the volume was made up with methanol to get a stock solution having a concentration of 100 µg/ml of Curcumin. From the stock solution, 2 ml was pipetted out in to a 100 ml volumetric flask and the volume was made up by methanol to obtain a concentration of 2 µg/ml solution of Curcumin.

Step-3: Five Soft Gel Capsules were weighed, then pricked and placed in a 500 ml beaker. 250 ml 0.1% w/v methanolic sodium carbonate was added to the beaker. The solutions were sonicated for 10 minutes followed by warming on water bath for 10 minutes. The solution was filtered through Whatman No 1 filter paper. The process was repeated for two times and the combined filtrates were taken in a 1000 ml volumetric flask. The volume was made up using methanol.

Phenomenex Gemini $C_{18}$ column (250×4.6 mm, 5µ ID) was used for HPLC analysis.

Mobile phase: 50 mM potassium dihydrogen phosphate (pH 3.5):Acetonitrile (40:60 v/v)

Figure 1A:
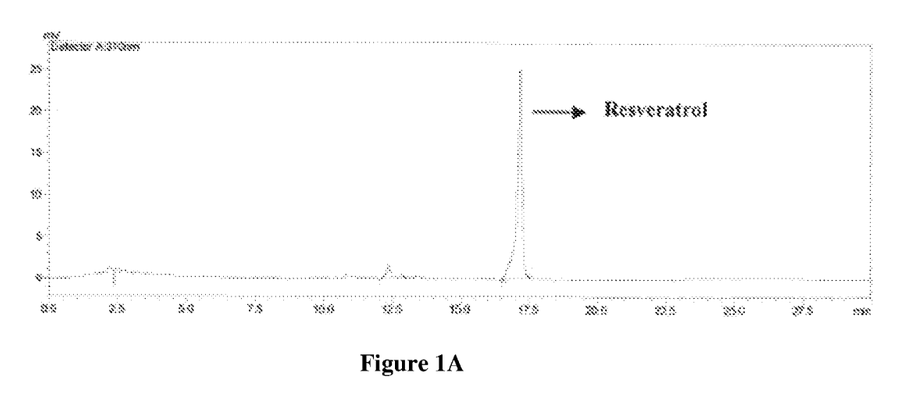
FIG. 1A illustrates the HPLC chromatogram of resveratrol standard.
Figure 1B:
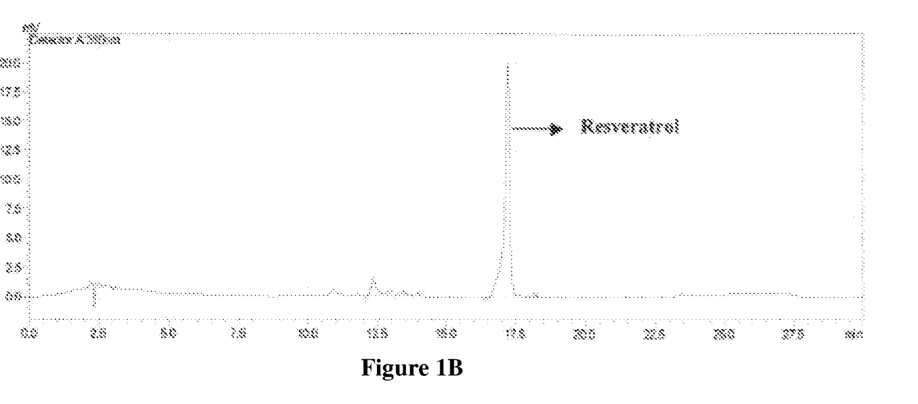
FIG. 1B illustrates the HPLC chromatogram of resveratrol active ingredient.
Figure 1C:
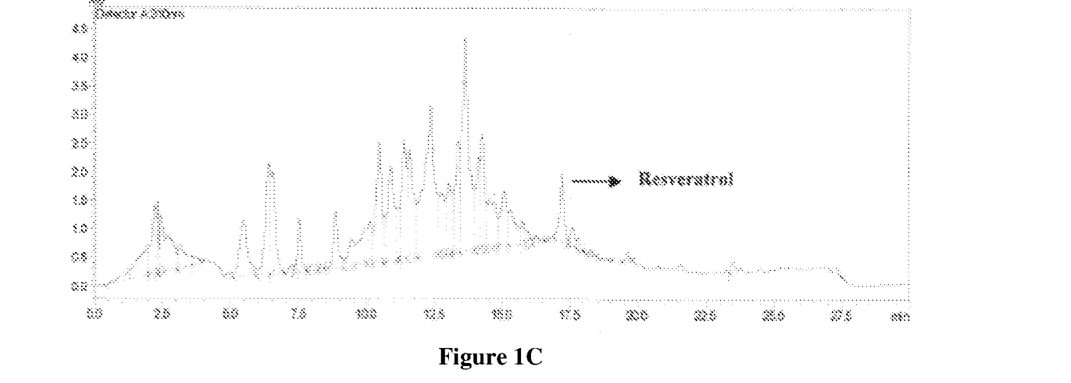
FIG. 1C illustrates the HPLC chromatogram of red wine extract.
Figure 1D:
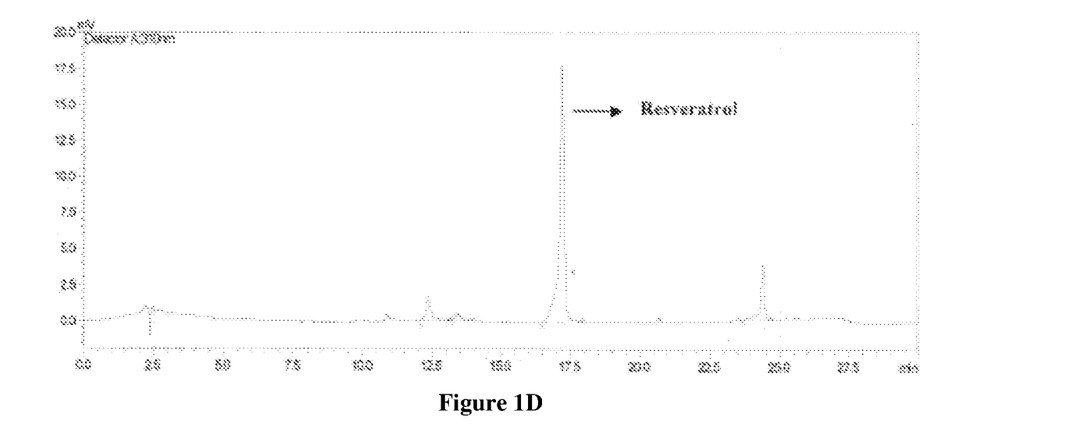
FIG. 1D illustrates the HPLC chromatogram of soft gel capsules (resveratrol)
Figure 2A:
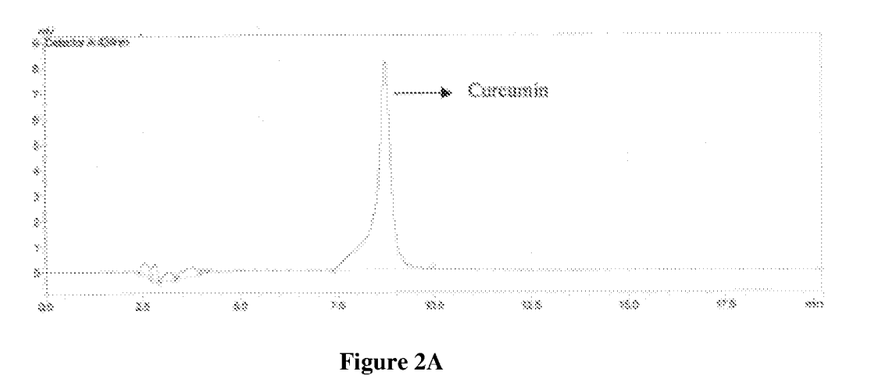
FIG. 2A illustrates the HPLC chromatogram of curcumin standard.
Figure 2B:
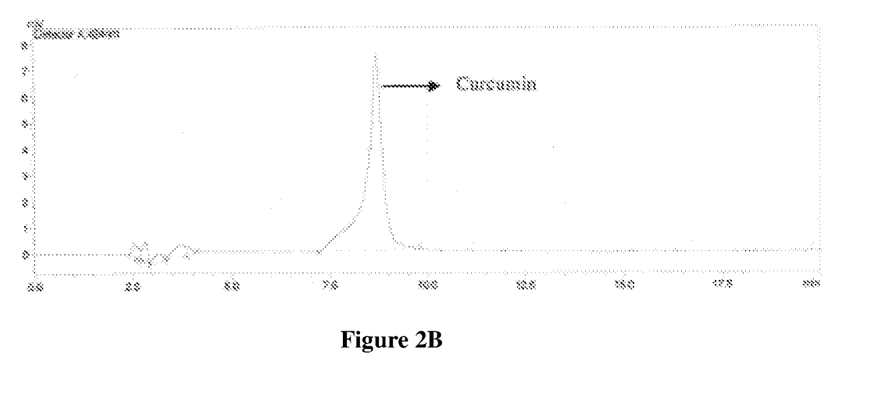
FIG. 2B illustrates the HPLC chromatogram of *Curcuma longa* dry extract.
Figure 2C:
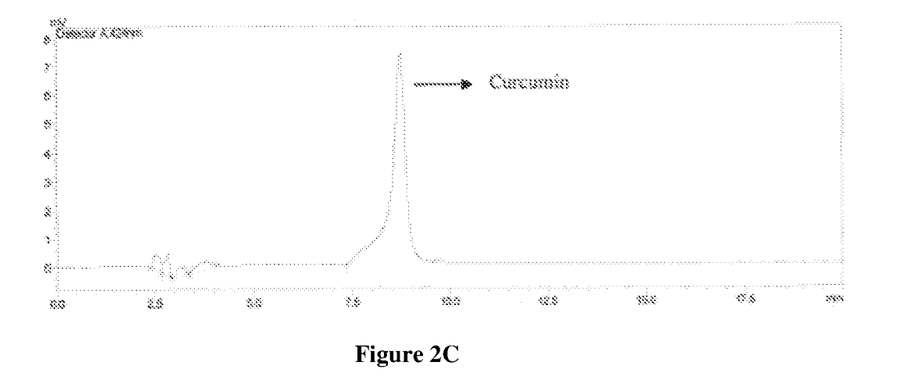
FIG. 2C illustrates the HPLC chromatogram of soft gel capsules (curcumin)

Flow rate: 0.8 ml per minute
Detection wavelength: 424 nm
Injection volume: 10 µl The HPLC chromatograms of the standard and samples are illustrated in FIGS. 2A, 2B and 2C. Curcumin was identified by its characteristic retention time.

EXAMPLE 3C: Analysis of AKBA

Step-1: 10 mg of AKBA standard (K. Patel Phyto Extracts Pvt. Ltd) was weighed and transferred into a 100 ml volumetric flask. 80 ml of methanol was added, shaken well to dissolve and the volume was made up with methanol to get a solution having a concentration of about 100 µg/ml of AKBA.

Step-2: 10 mg of *Boswellia* spp extract (B. No. KP/BS/008/14) was weighed and transferred quantitatively into a 100 ml volumetric flask. 80 ml of methanol was added, shaken well to dissolve and the volume was made up with methanol to get a solution having a concentration of about 100 µg/ml of *Boswellia* spp extract.

Step-3: Five Soft Gel Capsules were weighed, then pricked and placed in a 1000 ml beaker. 100 ml of methanol was added to the beaker. The solution was sonicated for 10 minutes followed by warming on a water bath for 10 minutes. The solution was filtered through Whatman No 1 filter paper. The process was repeated three times and the combined filtrates were taken in a 500 ml volumetric flask. The volume was made up using methanol.

Phenomenex Gemini $C_{18}$ column (250×4.6 mm, 5μ ID) was used for HPLC analysis.

Figure 3A:
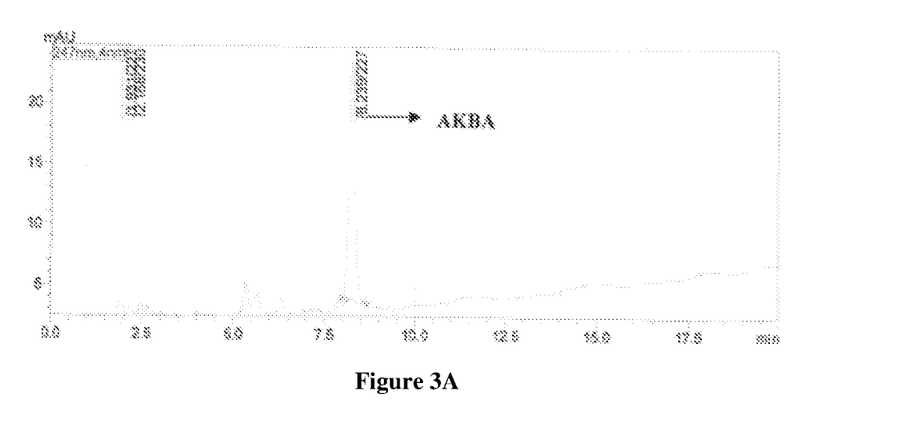
FIG. 3A illustrates the HPLC chromatogram of AKBA standard (30% purity)
Figure 3B:
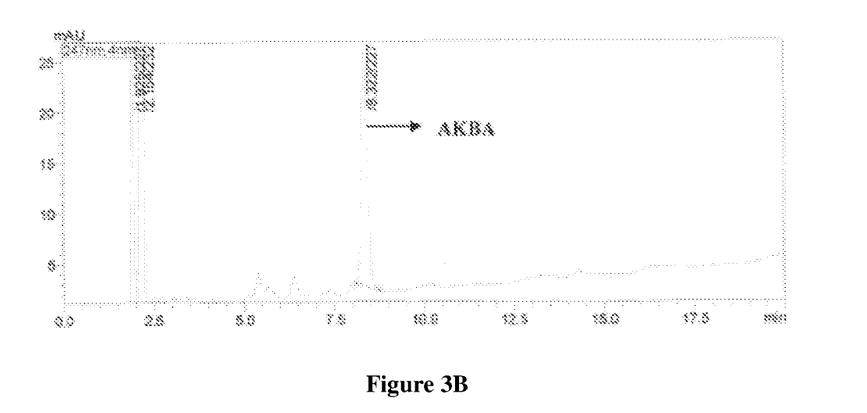
FIG. 3B illustrates the HPLC chromatogram of *Boswellia* spp extract.
Figure 3C:
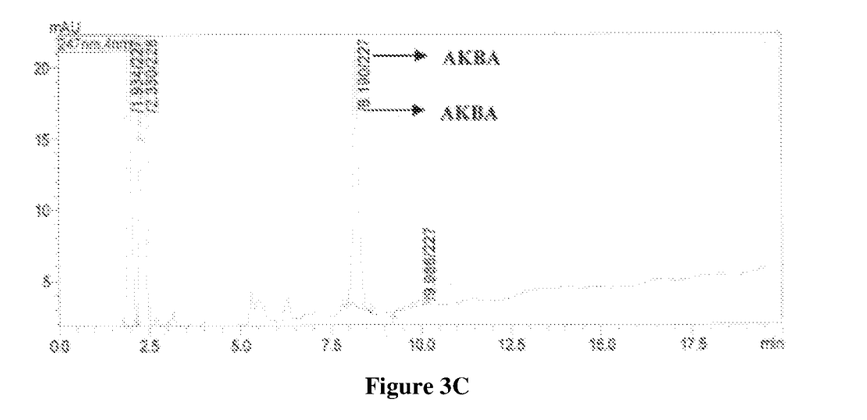
FIG. 3C illustrates the HPLC chromatogram of soft gel capsules (AKBA)

Mobile phase: Methanol:5% Acetonitrile in water (90:10 v/v); pH adjusted to 2.8 by dilute $H_3PO_4$ Flow rate: 1.5 ml per minute
Detection wavelength: 247 nm
Injection volume: 10 μl The HPLC chromatograms of the standard and samples are illustrated in FIGS. 3A, 3B and 3C. AKBA was identified by its characteristic retention time.

EXAMPLE 3D: Analysis of Limonene

Step-1: Samples of lemon and orange were purchased from local market. The rinds were carefully collected using a razor blade so that none of the white flesh under the rind was included in the sample. Then each sample was cut down to small pieces and 5 gm of each sample was extracted by 10 ml methanol by cold percolation using a magnetic stirrer for 15 minutes. The samples were filtered through Whatman No 1 filter paper into a 10 ml volumetric flask and the volume was made up by methanol.

Step-2: Five Soft Gel Capsules were weighed, then pricked and placed in a 100 ml beaker. 50 ml of methanol was added to the beaker. The solution was sonicated for 10 minutes followed by warming on a water bath for 10 minutes. The solution was filtered through Whatman No 1 filter paper. The solution was filtered through Whatman No 1 filter paper in to a 50 ml volumetric flask and the volume was made up using methanol.

Phenomenex Gemini $C_{18}$ column (250×4.6 mm, 5μ ID) was used for HPLC analysis.

Figure 4A:
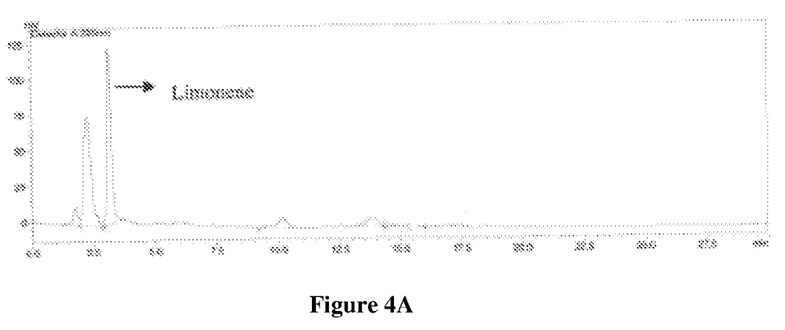
FIG. 4A illustrates the HPLC chromatogram of limonene (orange sample)
Figure 4B:
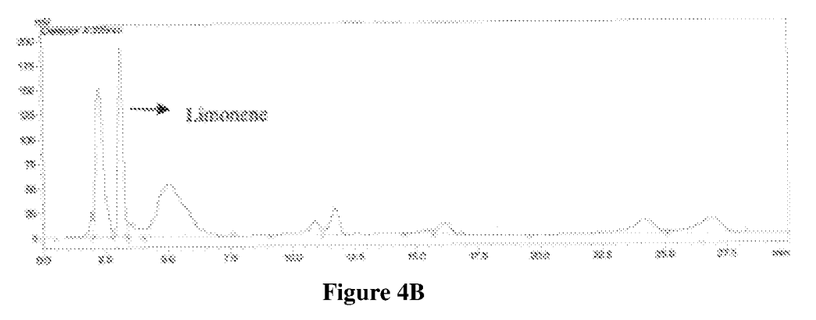
FIG. 4B illustrates the HPLC chromatogram of limonene (lemon sample)
Figure 4C:
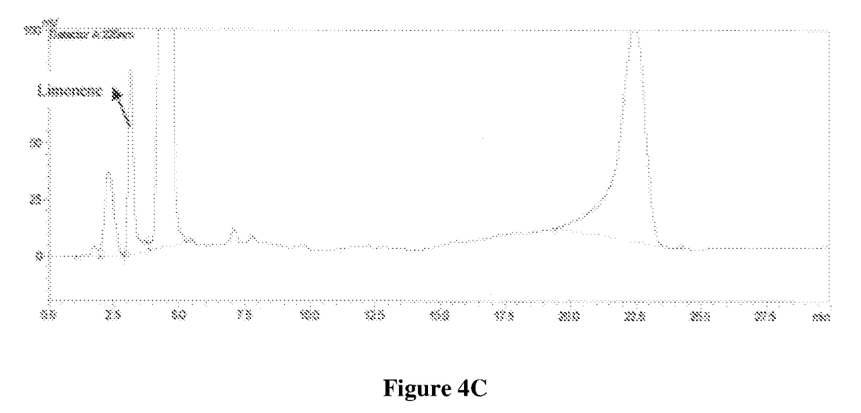
FIG. 4C illustrates the HPLC chromatogram of soft gel capsules (limonene).

Mobile phase: Acetonitrile:water (46:56 v/v)
Flow rate: 1.0 ml per minute
Detection wavelength: 225 nm
Injection volume: 10 μl The HPLC chromatograms of the standard and samples are illustrated in FIGS. 4A, 4B and 4C. Limonene was identified by its characteristic retention time.

The present invention would be now explained with the following anecdotal studies:

Anecdote 1: Effect of the Formulation on Prostate Cancer

The patient in this case was a 69 year old male. The pathology report indicated prostate cancer; the PSA was measured to be 185. The patient was initially started on a hormone therapy. There was no significant improvement in the patient at the end of 3 months. The patient was started on an additional therapy containing the formulation of the present invention along with the hormone therapy. The intake dosage of the formulation was 1000 mg per day. The treatment was continued for 90 days, during this period an improvement in the appetite and energy levels were observed. There was no side effect observed. A serum PSA of below 1 was reported on day 180.

The same dosage was continued for another 6 months, the serum level remained constant.

The dosage was then reduced to 750 mg per day. The lowered dosage was able to maintain the patient's healthy condition.

Anecdote 2: Effect of the Formulation on Prostate Epithelioma

A 74 year old male patient was diagnosed with malignant epithelioma of the prostate. Prostate Epithelioma was confirmed by elevated PSA level, manual examination and biopsy of the tumor. The patient was started on a treatment containing the formulation of the present invention. The formulation of the present invention was administered to the patient at a dosage of 750 mg, 2 times per day over a period of several months. There were no significant side effects observed. A reduction in the tumor size was observed after treatment with the formulation for six months. During this time there were no secondary symptoms of prostate neoplasia, also metastasis was not observed in the patient.

Anecdote 3: Effect of the Formulation on Cervical Carcinoma

A 53 year old female patient with cervical carcinoma was administered chemotherapy simultaneously with the formulation of the present invention. A dosage 1000 mg, 3 times per day of the formulation was administered initially for 3 months. There were no side effects or metastasis observed. There was a reduction in the size of the tumor. The treatment was continued for another 6 months, at the end of which there was a significant reduction in the growth. The patient was put on a reduced dosage for further 3 months.

Anecdote 4: Effect of the Formulation on Lung Cancer

A 66 year old female was diagnosed with lung cancer. The patient was started on chemotherapy. There was no response to chemotherapy, so the patient stopped the chemotherapy after a few months. The patient was started on the formulation of the present invention. The patient was given a dosage of 1200 mg per day in the form of soft gelatin capsules. After 6 months a decreased tumor activity was observed.

Anecdote 5: Effect of the Formulation on Ovarian Cancer

A 68 year old female was diagnosed with ovarian cancer. The patient was started with chemotherapy; and the formulation of the present invention was started as an adjuvant to the chemotherapy. A reduction in the growth was observed after 4 months of treatment with the formulation if the present invention. This proves that the formulation of the present invention is effective as an adjuvant to chemotherapy.

Anecdote 6: Effect of the Formulation on Prostate Cancer

A male patient aged 77 complaining of urinary outflow obstruction and low backache was diagnosed with prostate cancer. The diagnosis was confirmed by urological examination, an elevated serum PSA level (94), MRI scan and biopsy. The patient was started on a treatment of soft gelatin capsules containing the formulation of the present invention. A dosage of 1000 mg per day was administered to the patient. The serum PSA levels were monitored regularly. There was a consistent lowering of the serum PSA levels with the progression of the therapy. After 6 months a serum PSA of 2 was observed. Also, an improvement in the quality of the life of the patient was observed. There was no significant side effect observed, since the initiating the therapy.

Anecdote 7: Effect of the Formulation on Breast Cancer

A 54 year old female patient with recurring breast cancer with metastasis was started on a treatment comprising the formulation of the present invention. After 6 months normal values for CEA, CA-15-3, NCCST439 were observed. The patient has not shown any signs of recurrence and is leading a healthy life.

Anecdote 8: Effect of the Formulation on Oral Cancer

A 46 year old male having a low grade neoplasm of the oral cavity was administered the formulation of the present invention. An oral dosage of 750 mg per day was administered to the patient for 3 weeks. A reversal in the growth of the neoplasm was observed at the end of 3 weeks.

Anecdote 9: Effect of the Formulation on Prostate Cancer

A 65 year old male patient diagnosed with prostate cancer not responding to chemotherapy and hormone treatment was administered the formulation of the present invention. An oral dosage in the form of soft gelatin capsules containing the formulation of the present disclosure, 750 g, 3 times per day was given to the patient. A 82% reduction in the serum PSA was observed in the patient at the end of 6 weeks. Thromboembolic side effects were not observed.

Anecdote 10: Effect of the Formulation on Oral Cancer

A 36 years old male patient was diagnosed with oral cancer. The cancer was confirmed by manual examination and biopsy of the tumor. The patient was administered soft gelatin capsule containing the formulation of the present invention. The dosage was 750 mg per day. The course of treatment lasted several months, resulting in no significant side effects. The patient experienced a reversal in the growth rate of the tumor cells, death of the existing tumor cells, reduction in the tumor size and no metastasis of the tumor. The patient exhibited no secondary symptoms of oral cancer on continuing the treatment. Also, there were no long term side effects of the treatment or metastasis of the tumor exhibited by the patent.

TECHNICAL ADVANCES

The present disclosure provides a phyto-active based formulation that can arrest the growth of cancerous cells.

The present disclosure provides a phyto-active based formulation that can arrest the growth of cancerous cells with minimum side effects.

The present disclosure also provides a phyto-active based formulation which can enhance or support the therapeutic efficacy of an existing drug.

The exemplary embodiments herein quantify the benefits arising out of this disclosure and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A formulation for treating prostate cancer, breast cancer, uterine cancer, ovarian cancer, lung cancer and kidney cancer; said formulation having active constituents comprising a combination of:
    a. 60 to 80% wt of *Boswellia* spp extract;
    b. 10 to 30% wt of *Curcuma longa* extract; and
    c. 5 to 20% wt of *Vitis vinifera* extract.

2. The formulation of claim 1 having active constituents comprising a combination of: 70 wt % of *Boswellia* spp extract; 20 wt % of *Curcuma longa* extract; and 10 wt % of *Vitis vinifera* extract.

3. The formulation of claim 1, wherein said *Boswellia* spp extract comprises 60 to 65% boswellic acid, and 5 to 20% limonene.

4. The formulation of claim 3, wherein said boswellic acid is selected from the group consisting of acetyl keto boswellic acid (AKBA), keto boswellic acid (KBA) and a combination thereof wherein the boswellic acid contains 30-40% of AKBA and KBA.

5. The formulation of claim 1, wherein said *Curcuma longa* extract comprises 85 to 95% curcuminoids.

6. The formulation of claim 1, wherein said *Vitis vinifera* extract comprises 20 to 40% polyphenol resveratrol.

7. The formulation of claim 1, wherein said formulation is in a dosage form selected from the group consisting of a tablet, a capsule, liquid, syrup, powder, a pill, a lozenge, a pastille, and soft gelatin capsule.

8. The formulation of claim 1, wherein each dose of said formulation is 750 to 1500 mg in mass, administered 3 to 4 times per day.

9. A method for treating prostate cancer, breast cancer, uterine cancer, ovarian cancer, lung cancer and kidney cancer in a subject, said method comprising orally administering to a subject a therapeutically effective amount of a formulation having active constituents comprising a combination of:
    a. 60 to 80 wt % of *Boswellia* spp extract;
    b. 10 to 30 wt % of *Curcuma longa* extract; and
    c. 5 to 20 wt % of *Vitis vinifera* extract.

10. The method of claim 9, wherein the therapeutically effective amount of said formulation is 750 to 1500 mg in mass administered 3 to 4 times per day.

11. The method of claim 9, wherein the therapeutically effective amount of formulation administered is 12.5 mg per kg of body weight 3 to 4 times per day.

12. The method of claim 9, wherein the formulation is in a dosage form selected from the group consisting of a tablet, a capsule, liquid, syrup, powder, a pill, a lozenge, a pastille, and a soft gelatin capsule.

* * * * *